US 6,564,097 B1

(12) United States Patent
Williams et al.

(10) Patent No.: US 6,564,097 B1
(45) Date of Patent: May 13, 2003

(54) METHODS FOR SENSING ARRHYTHMIAS IN A PACEMAKER/DEFIBRILLATOR AND A PACEMAKER/DEFIBRILLATOR PROGRAMMED TO IMPLEMENT THE SAME

(75) Inventors: Michael O. Williams, Mt. Shasta, CA (US); Timothy Olson, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 10/251,282

(22) Filed: Sep. 20, 2002

Related U.S. Application Data

(62) Division of application No. 09/972,214, filed on Oct. 4, 2001, now Pat. No. 6,484,058, which is a division of application No. 09/442,832, filed on Nov. 17, 1999, now Pat. No. 6,324,422.

(51) Int. Cl.$^7$ .............................................. A61N 1/362
(52) U.S. Cl. ....................................................... 607/14
(58) Field of Search ............................ 607/4–5, 9, 14, 607/15, 17; 600/510

(56) References Cited

U.S. PATENT DOCUMENTS

| 3,648,707 A | | 3/1972 | Greatbatch .............. 128/419 P |
|---|---|---|---|
| 4,059,116 A | | 11/1977 | Adams ................. 128/129 PG |
| 4,503,857 A | | 3/1985 | Boute et al. .......... 128/419 PG |
| 4,554,921 A | | 11/1985 | Boute et al. .......... 128/419 PG |
| 4,624,260 A | * | 11/1986 | Baker et al. .................. 607/14 |
| 4,788,980 A | * | 12/1988 | Mann et al. .................. 607/14 |
| 4,920,925 A | | 5/1990 | Korenberg et al. ... 128/419 PG |
| 4,974,589 A | * | 12/1990 | Sholder .......................... 607/9 |
| 5,129,393 A | | 7/1992 | Brumwell ............. 128/419 PG |
| 5,470,342 A | | 11/1995 | Mann et al. .................... 607/5 |
| 5,788,717 A | * | 8/1998 | Mann et al. .................. 607/14 |
| 5,792,192 A | | 8/1998 | Lu .............................. 607/14 |
| 5,814,083 A | * | 9/1998 | Hess et al. .................... 607/14 |
| 6,337,996 B1 | * | 1/2002 | Legay et al. .................. 607/14 |

OTHER PUBLICATIONS

Provenier, et al.; The Automatic Mode Switch Function in Successive Generations of Minute Ventilation Sensing Dual Chamber Rate Responsive Pacemakers; Pace, vol. 17; Nov. 1994; Part II; pp. 1913–1919.

Telectronics Pacing Systems; Meta DDDR Model 1250 H Multiprogrammable, Minute Ventilation Rate Responsive Pulse Generator with Telemetry Physician's Manual; pp. i–82.

* cited by examiner

Primary Examiner—Kennedy Schaetzle
Assistant Examiner—Kristen Droesch
(74) Attorney, Agent, or Firm—Steven M. Mitchell

(57) ABSTRACT

A method for detecting an arrhythmia hidden by rapid pacing in a rate adaptive pacemaker/defibrillator. Unmasking a potential arrhythmia is accomplished by lengthening the pace cycle length by a small amount for a number of cycles followed by a shortening of the pace cycle length for the same number of cycles giving an average pacing rate equivalent to the desired rate. This can occur at all times or only when conditions make arrhythmia masking possible. Changing the pace cycle by a small amount over a number of cycles will move the arrhythmia and paced rhythm out of synchronization. Forcing the pacer to continue sensing the arrhythmia is accomplished by insuring that the pacer's sense refractory is less than one half of the pacing cycle length. This is done by constraining the programming of that value to one half the minimum pacing cycle length or using an adaptive sense refractory period. In another embodiment, a hidden arrhythmia is detected by periodically checking a relative refractory portion of the pace refractory period to see if a signal indicative of arrhythmia can be detected. This relative refractory period is produced by shortening the established refractory period by a calculated adaptive relative refractory period.

11 Claims, 12 Drawing Sheets

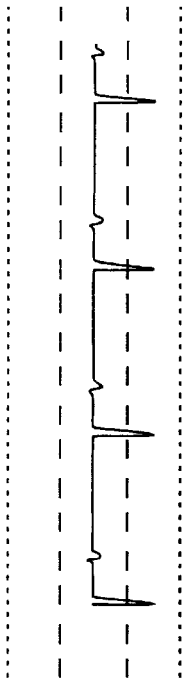
Fig. 7A  VENTRICULAR IEGM
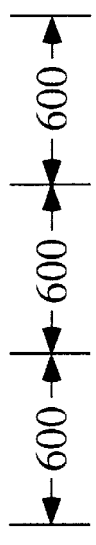
Fig. 7B  TIME (MS)
Fig. 7C  DEFIB VRP
Fig. 7D  PACER VRP

VENTRICULAR
IEGM

600 — 600 — 700 — 600

TIME (MS)

ADAPTIVE RELATIVE
REFRACTORY

100

DEFIB
VRP

PACER
VRP

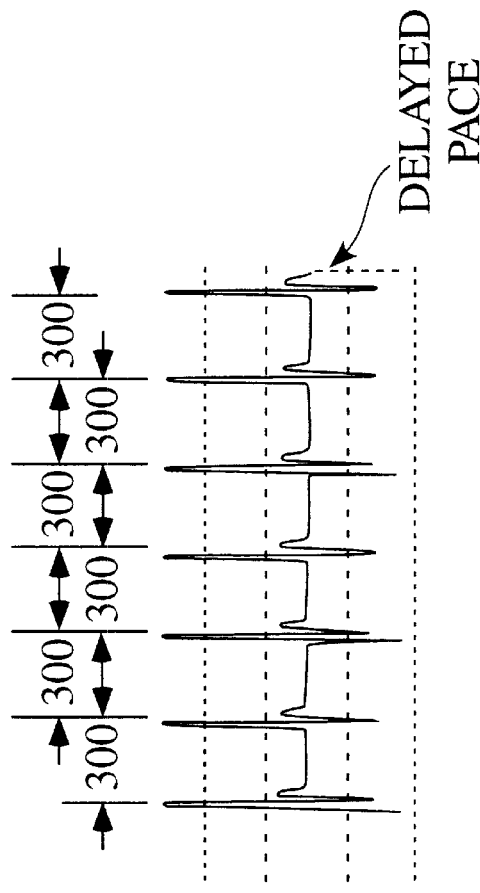
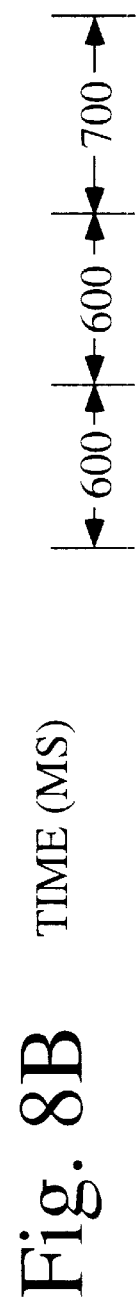
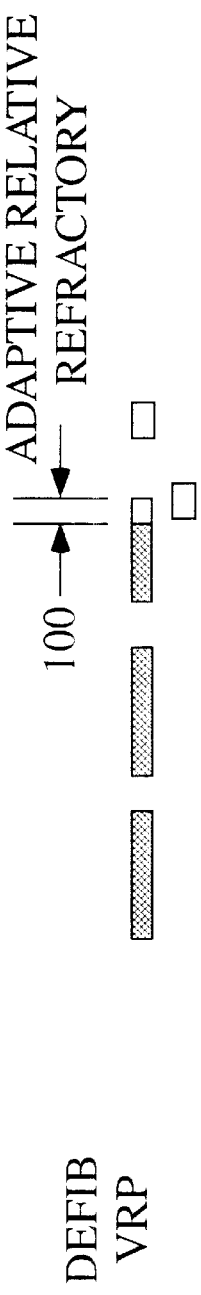
Fig. 8A  VENTRICULAR IEGM
Fig. 8B  TIME (MS)
Fig. 8C  DEFIB VRP
Fig. 8D  PACER VRP

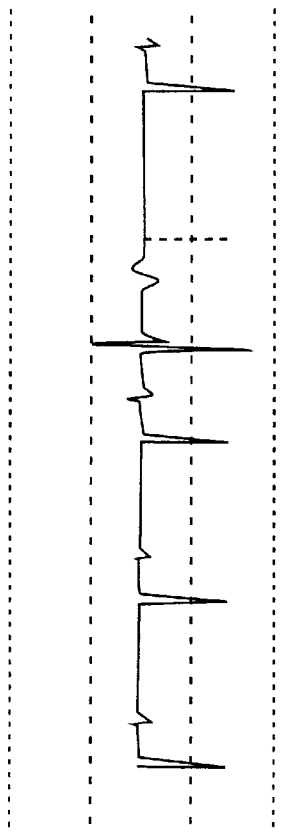
Fig. 8E VENTRICULAR IEGM
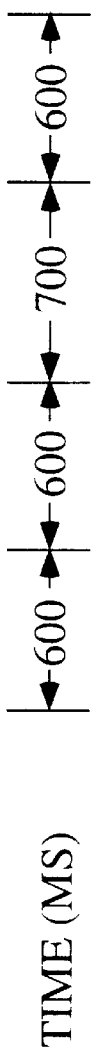
Fig. 8F TIME (MS)
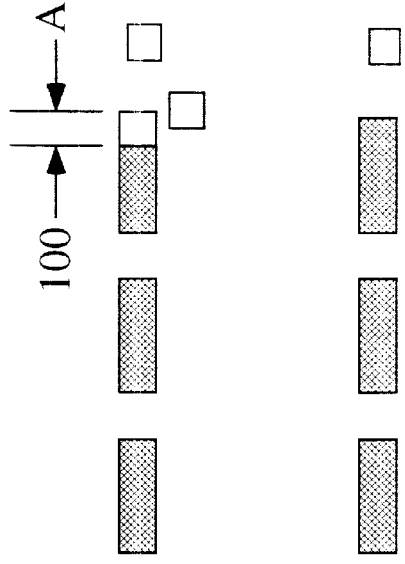
Fig. 8G DEFIB VRP
Fig. 8H PACER VRP

METHODS FOR SENSING ARRHYTHMIAS IN A PACEMAKER/DEFIBRILLATOR AND A PACEMAKER/DEFIBRILLATOR PROGRAMMED TO IMPLEMENT THE SAME

This is a divisional of application Ser. No. 09/972,214, filed on Oct. 4, 2001, now U.S. Pat. No. 6,484,058, which is a division of application Ser. No. 09/442,832, filed Nov. 17, 1999, now U.S. Pat. No. 6,324,422.

BACKGROUND OF THE INVENTION

The present invention relates generally to implantable cardiac therapy devices, and more particularly, to improved methods for sensing arrhythmias in a pacemaker/defibrillator, and a pacemaker/defibrillator configured or programmed to implement the same.

Implantable cardioverter defibrillators (ICDs) are sophisticated medical devices which are surgically implanted (abdominally or pectorally) in a patient to monitor the cardiac activity of the patient's heart, and to deliver electrical stimulation as required to correct cardiac arrhythmias which occur due to disturbances in the normal pattern of electrical conduction within the heart muscle.

Cardiac arrhythmias can generally be thought of as disturbances of the normal rhythm of the heart beat. Cardiac arrhythmias are broadly divided into two major categories, namely, bradyarrhythmia and tachyarrhythmia. Tachyarrhythmiacan be broadly defined as an abnormally rapid heart rate (e.g., over 100 beats/minute, at rest), and bradyarrhythmia can be broadly defined as an abnormally slow heart rate (e.g., less than 50 beats/minute).

Tachyarrhythmias are further subdivided into two major sub-categories, namely, tachycardia and fibrillation. Tachycardia is a condition in which the electrical activity and rhythms of the heart are rapid, but organized. Fibrillation is a condition in which the electrical activity and rhythm of the heart are rapid, chaotic, and disorganized. Tachycardia and fibrillation are further classified according to their location within the heart, namely, either atrial or ventricular.

A depolarization signal, which is a small electrical impulse, triggers contraction of the myocardial tissue of the human heart. In this regard, the beating of a human heart is manifested by depolarization signals corresponding to the contraction of the atria, referred to as P-waves, and to the contraction of the ventricles, referred to as R-waves. The complex of depolarization signals produced by a normal heart beat is commonly referred to as the PQRS or QRS complex. The sequence of PQRS complexes produced by a beating heart constitutes an electrogram or electrocardiogram signal (depending upon whether the signal is detected within or outside of the heart, respectively) that can be monitored by appropriate electrical circuitry to determine the condition of the heart.

In general, an implantable pacemaker includes sensing circuitry which monitors the heart by analyzing electrograms (EGMs) detected by endocardial (intracardiac) sensing electrodes positioned in or adjacent to the patient's heart, and pacing circuitry that delivers anti-bradycardia pacing pulses to the heart upon detection of bradycardia, in order to thereby stimulate or pace the heart back into a normal sinus rhythm. More particularly, if the heart does not beat naturally (on its own) within a prescribed time period, (i.e., if an intrinsic heart beat is not detected within a prescribed time period), then an electrical stimulation pulse (pacing pulse) is provided to force the heart muscle tissue to contract, thereby assuring that a prescribed minimum heart rate is maintained. Dual-chamber pacemakers are capable of detecting either atrial or ventricular bradycardia, and delivering the appropriate atrial and/or ventricular anti-bradycardia pacing pulses as required.

In general, an ICD continuously monitors the heart activity of the patient in whom the device is implanted by analyzing electrograms (EGMs) detected by endocardial (intracardiac) sensing electrodes positioned in the right ventricular apex and/or right atrium of the patient's heart. Contemporary ICDs are generally capable of diagnosing the various types of cardiac arrhythmias discussed above, and then delivering the appropriate electrical stimulation/therapy to the patient's heart to thereby correct or terminate the diagnosed arrhythmia. As used herein, the terminology "implantable cardioverter defibrillator" (ICD) is intended to encompass these and other forms and types of implantable cardiac therapy devices.

It is common in implantable cardiac stimulation devices such as pacemakers and ICDs to employ "refractory periods" during which the sensing circuits of the device are inhibited in order to prevent false detection of a cardiac depolarization. More particularly, refractory periods are necessary in such implantable cardiac stimulation devices in order to prevent "oversensing". Oversensing is a phenomenon in which a normal cardiac event associated with a depolarization, such as the repolarization of cardiac tissue, referred to as the T-wave, or an afterpotential generated by a paced depolarization, is sensed and incorrectly determined to be a separate and natural depolarization. Thus, the "refractory period" is defined as the period of time immediately following a natural or induced depolarization during which sensing is inhibited in order to prevent oversensing.

U.S. Pat. No. 3,648,707, issued to Greatbatch, discloses a dual-chamber rate responsive pacemaker which is adapted to operate in an atrial synchronous mode. This type of pacemaker is generally referred to in the art as a "VDD" pacemaker. The Greatbatch pacemaker includes electrodes for sensing contractions of the atrium and ventricle, and a pulse generator for pacing the ventricle. After sensing a contraction of the ventricle or pacing the ventricle, a lower rate timer is restarted. If this timer expires, it triggers generation of a ventricular pacing pulse. The Greatbatch pacemaker also includes an A–V interval timer, initiated in response to the sensing of an atrial contraction. On expiration of the timer, the ventricular pacing pulse is triggered. The Greatbatch pacemaker also includes a third timer, defining an upper rate interval initiated following ventricular pacing or sensing of a ventricular contraction. During the upper rate interval, time out of the A–V interval will not trigger a ventricular pacing pulse. This allows for inhibition of the ventricular pulse generator in the event that a natural atrial contraction follows a ventricular contraction. The Greatbatch pacemaker also uses a maximum synchronous pacing rate corresponding to the upper rate interval. If the atrial rate exceeds this rate, the pacing rate is lowered to the higher of one-half of the sensed atrial rate or the rate determined by the lower rate timer. In this way, pacemaker induced or mediated tachycardias (PMTs) are prevented.

U.S. Pat. No. 4,059,116, issued to Adams, discloses a VDD dual-chamber rate responsive pacemaker which, rather than preventing generation of a ventricular stimulus in response to time out of the A–V interval during the upper rate interval, instead delays the ventricular stimulus until the expiration of the upper rate interval. In addition, the Adams pacemaker utilizes a post-ventricularatrial refractory period (PVARP) after each ventricular pacing pulse and each sensed ventricular contraction, during which an atrial contraction does not initiate timing of the A–V interval. Because of these features, the Adams pacemaker exhibits an improved response to atrial contractions occurring at intervals less than the upper rate interval. The Adams pacemaker was programmed to generate ventricular stimulation pulses separated by the upper rate interval, displaying gradually lengthening A–V intervals until an atrial contraction fell within the post-ventricular atrial refractory period. The Adams pacemaker would then resynchronize on the next subsequent atrial contraction, mimicking the natural condition known as Wenckebach behavior. In commercially marketed pacemakers employing the Adams invention, the behavior of the pacemaker in the presence of high natural atrial rates is referred to as "Pseudo-Wenckebach" upper rate behavior.

Numerous other dual-chamber pacemakers have been proposed which vary their post-ventricular atrial refractory periods (PVARPs) in an attempt to prevent PMTs. For example, U.S. Pat. No. 4,920,965, discloses a dual-chamber pacemaker in which a post-ventricularatrial refractory interval is calculated based upon the time of occurrence of the atrial contraction, relative to the preceding ventricular pacing pulse or sensed ventricular contraction. The post-ventricular atrial refractory period is gradually decreased in response to increasing natural atrial rates. Alternatively, it has been suggested to monitor the timing of atrial contractions with respect to previous ventricular contractions and if their timing indicates that the atrial contractions are probably retrograde P-waves, to extend the post-ventricular atrial refractory period beyond the measured time of occurrence of the retrograde P-waves. Such pacemakers are disclosed in U.S. Pat. Nos. 4,544,921 and 4,503,857, both issued to Boute et al.

U.S. Pat. No. 5,129,393, issued to Brumwell, discloses a VDD dual-chamber rate responsive pacemaker equipped with an integral activity sensor for monitoring the physical activity level of the heart patient. The pacing rate of the Brumwell pacemaker is regulated in response to the patient's need for cardiac output, in response to the output of the integral activity sensor, and is adapted to operate in an atrial synchronous mode. The post-ventricular atrial refractory period (PVARP) is calculated in response to both the sensor-determined ventricular pacing rate and the natural atrial rhythm. The ventricular pacing rate will thus follow a high natural atrial rate, even in the presence of an indication by the sensor of low physical activity. In particular, the PVARP is calculated by determining the average interval separating natural atrial contractions (average A—A interval) and the average interval separating paced or sensed ventricular contractions (average V—V interval). An interval equal to a predetermined portion (e.g., 75%) of the A—A interval (A—A ARP) and an interval corresponding to a predetermined portion (e.g., 75%) of the V—V interval (V—V ARP) are calculated. The V—V ARP and A—A ARP are compared, and the lesser of the two intervals are employed as a variable PVARP.

In addition, an article entitled 'The "Automatic Mode Switch" Function in Successive Generations of Minute Ventilation Sensing Dual Chamber Rate Responsive Pacemakers' (F. Provenier et al., PACE, Vol. 17, pps. 1913–19 (November, 1994)) discloses automatic switching from DDDR to VVIR pacing modes when a selected number of atrial events are sensed by automatic mode switching (AMS) circuitry. According to the article, a PVARP adapts continuously to changes in metabolic indicated rate (MIR) determined by a sensor such as a ventilation sensor. It will be appreciated that the adaptive PVARP includes a blanking period of a predetermined length, e.g., 100 milliseconds. The pacemaker thus is configured so as to permit sensing during the later stages of the PVARP. A refractory period as discussed in the article is defined as consisting of an absolute refractory period (the blanking period) and a relative refractory period (that portion in which sensing of atrial events can occur).

Although the above-discussed dual-chamber pacemakers are generally effective at preventing or terminating PMTs, and/or at adaptively varying the PVARP to allow sensing of fast native atrial rates, while ensuring adequate atrial and ventricular anti-bradycardia pacing, because they do not deliver either atrial or ventricular defibrillation therapy, they are not concerned with the underdetection of either atrial or ventricular tachyarrhythmias.

Single-chamber ICDs are designed to detect and treat only ventricular arrhythmias, and not to detect and treat atrial arrhythrnias. If a given patient has a cardiac condition which requires both atrial anti-bradycardia pacing and treatment of ventricular arrhythmias, it is possible that both an implantable pacemaker and an ICD would be separately implanted. Obviously, the cost of these separate devices and the cost and risk of the required separate implantation procedures is much greater than would be the cost and risk associated with the implantation of a single device which could perform the functions of both the pacemaker and the ICD. In addition, some ICDs do not allow the pacing rate to vary according to a patient's hemodynamic requirements. This forces pacing rates in these ICDs to remain fairly slow, e.g. 30–70 pulses per minute. Currently available pacemakers can pace at higher rates, e.g. 150 pulses per minute, when the patient requires it. This is desirable for patient health and well-being. For these reasons, one of the major areas of R&D within the field of ICDs is the development of dual-chamber ICDs which are capable of detecting and treating both atrial and ventricular arrhythmias.

In general, it will be appreciated that a dual-chamber ICD has two primary functions. The first primary function is to provide both atrial and ventricular anti-bradycardia pacing, as required, in order to ensure that an appropriate heart rate is maintained. The second primary function is to detect atrial and ventricular tachyarrhythmias and deliver the appropriate cardiac therapy, as required. However, the first and second primary functions conflict when moderate to high rates of pacing are required, since moderate to high pacing rates require that the device be refractory for a significant portion of the time during the periods when such moderate to high pacing rates are required. This refractoriness can result in undersensing or delayed detection of atrial and/or ventricular tachyarrhythmias. For the sake of simplicity, the ensuing discussion will be directed to the issue of undersensing or delayed detection of ventricular tachyarrhythmias. However, it should be appreciated that the ensuing discussion and the present invention are equally applicable to the issue of undersensing or delayed detection of atrial tachyarrhythmias, or most broadly, to any single-chamber of dual-chamber pacemaker/defibrillator in which undersensing or delayed detection of any type of arrhythmia that may be hidden by pacing is an issue.

Two factors can bear on a solution to this problem of conflicting goals in an ICD capable of high pacing rates. The first factor is whether the pacemaker (or "pacer") section and defibrillator (or "defib") section share the same circuitry for sensing ventricular cardiac events. The second factor is whether the pacer and defib sections share the same ventricular sense refractory periods. These two factors create four possible machine types which may use different methods to solve this problem.

Four different types of dual-chamber ICD are proposed. In a first type of dual-chamber ICD, the pacemaker and defibrillator sections share the same circuitry for sensing ventricular cardiac events and use the same ventricular sense refractory periods. In a second type of dual-chamber ICD, the pacemaker and defibrillator sections utilize completely independent circuitry for sensing ventricular cardiac events and use completely independent ventricular sense refractory periods. In a third type of dual-chamber ICD, the pacemaker and defibrillator sections share the same circuitry for sensing ventricular cardiac events, but use different ventricular sense refractory periods. In a fourth type of dual-chamber ICD, the pacemaker and defibrillator sections utilize completely independent circuitry for sensing ventricular cardiac events but use the same ventricular sense refractory periods. The essence of sharing the sensing circuitry between the pacemaker and defibrillator sections is that the threshold used for sensing intrinsic cardiac events is always the same for both pacemaker and defibrillator sections, i.e. they see the same cardiac events when neither are refractory.

An exemplary dual-chamber ICD of the first type is disclosed in U.S. Pat. No. 5,007,422, issued to Pless et al., which patent is commonly assigned to the assignee of the present invention and which patent is herein incorporated by reference. It will be readily appreciated by those skilled in the pertinent art that the dual-chamber ICD disclosed in the Pless et al. patent can be easily programmed to function as a dual-chamber ICD of the second type. Different methods of operating the dual-chamber ICD disclosed in the Pless et al. patent are disclosed in U.S. Pat. Nos. 5,111,816 and 5,048,521, which patents are commonly assigned to the assignee of the present invention and which patents are also incorporated herein by reference. However, when the dual-chamber ICD disclosed in the Pless et al. patent is programmed to function as a device of the first type or programmed to function as a device of the third type, it is possible that ventricular arrhythmias would be masked or concealed due to the occurrence of such ventricular arrhythmias during the pace refractory period, and not during the "alert period" (i.e., non-refractory period) when the sense circuitry is active (i.e., not inhibited).

An exemplary dual-chamber ICD of the second type is disclosed in U.S. Pat. No. 5,470,342, issued to Mann et al., which patent is commonly assigned to the assignee of the present invention and which patent is herein incorporated by reference. More particularly, the Mann et al. dual-chamber ICD utilizes two parallel signal processing channels for sensing depolarization signals sensed over a single sensing lead (or lead network), each processing channel having its own independently programmable refractory period, and each signal processing channel further having its own independently adjustable gain and/or threshold setting. It will be readily appreciated by those skilled in the pertinent art that the dual-chamber ICD disclosed in the Mann et al. patent can be easily programmed to function as a dual-chamber ICD of the fourth type. The Mann et al. dual-chamber ICD is programmed to adaptively adjust the respective refractory periods, and/or gain/threshold settings of the respective processing channels in such a manner as to optimally sense: (1) cardiac depolarizations, whether associated with natural cardiac rhythm or tachyarrhythmias; or, (2) fibrillation. However, the Mann et al. dual-chamber ICD does not fully resolve the problem described above, i.e., it is still possible that ventricular arrhythmias would be masked or concealed due to non-occurrence of a single ventricular arrhythmic event within the alert period during moderate to high rates of pacing.

Therefore, based on the above and foregoing, it can be appreciated that there presently exists a need in the art for improved methods for sensing arrhythmias in a pacemaker/defibrillator which overcome the above-described drawbacks and shortcomings of the existing methods, and a pacemaker/defibrillator programmed to implement the same.

SUMMARY OF THE INVENTION

The present invention encompasses, in one of its embodiments, a method of detecting an arrhythmia hidden by pacing in a pacemaker/defibrillator, including the steps of:

(a) increasing a pace cycle length and delaying a next occurring pacing pulse by the increased pace cycle length;

(b) analyzing a sensed cardiac signal to determine the presence of an arrhythmia;

(c) repeating steps (a) and (b) a plurality of times;

(d) decreasing the pace cycle length and advancing the next occurring pacing pulse by the decreased pace cycle length;

(e) analyzing the sensed cardiac signal to determine the presence of an arrhythmia;

(f) repeating steps (d) and (e) a plurality of times;

wherein steps (a)–(f) are performed in a manner so that an average pace cycle length achieved over a period spanning steps (a) through (f) is equal to a desired pace cycle length.

The present invention encompasses, in another of its embodiments, a method of detecting an arrhythmia hidden by pacing in a pacemaker/defibrillator, including the steps of:

(a) increasing a pace cycle length by an amount x;

(b) analyzing a sensed cardiac signal to determine the presence of an arrhythmia;

(c) repeating steps (a) and (b) a plurality V of times;

(d) decreasing the pace cycle length by an amount y;

(e) analyzing the sensed cardiac signal to determine the presence of an arrhythmia;

(f) repeating steps (d) and (e) a plurality Z of times;

wherein steps (a)–(f) are performed in a manner so that an average pace length achieved over a period spanning steps (a) through (f) is equal to a desired pace cycle length.

The method, according to this embodiment, preferably further includes the step of setting a pacer sense refractory period to a value not greater than one half of the pace cycle length, once a hidden arrhythmia has been unmasked. This step can be implemented by setting the pacer sense refractory period to a value that does not exceed one half of the minimum pacing cycle length (CL), or by adaptively varying the pacer sense refractory period in response to variations in cardiac rate in such a manner as to ensure that the pacer sense refractory period does not exceed one half of the pace cycle length.

The present invention, in still another of its embodiments, encompasses a method of detecting an arrhythmia hidden by pacing in a pacemaker/defibrillator, including the steps of:

periodically checking cardiac activity during a relative refractory portion of a pace refractory period for a cardiac signal indicative of a cardiac event; and, if a cardiac signal is detected during the periodically checking step, then delaying a next occurring pacing pulse by an extension period.

The method, according to this embodiment, preferably further includes the step of additionally checking cardiac activity during the extension period for a further cardiac signal indicative of a cardiac event. If a cardiac signal is detected during the periodically checking step, and a further cardiac signal is detected during the extension period, then the cardiac event is determined to be a hidden arrhythmia. If a cardiac signal is not detected during the periodically checking step, then the next occurring pacing pulse is delivered without any delay.

The present invention, in yet another of its embodiments, encompasses a method of detecting an arrhythmia hidden by pacing in a pacemaker/defibrillator, including the steps of:
periodically checking cardiac activity during a relative refractory portion of a pace refractory period for a cardiac signal indicative of a potential arrhythmic cardiac event;
if a cardiac signal is detected during the periodically checking step, then checking cardiac activity during the relative refractory portion each of a plurality of consecutive pace refractory periods for a further cardiac signal indicative of a potential arrhythmic cardiac event; and,
if a further cardiac signal is detected during each of the plurality of consecutive pace refractory periods, then delaying a next occurring pacing pulse by an extension period.

The method, according to this embodiment, preferably further includes the step of additionally checking cardiac activity during the extension period for an additional cardiac signal indicative of a potential arrhythmic cardiac event. If a cardiac signal is detected during the extension period, then the cardiac event is determined to be a hidden arrhythmia. Alternatively, the method, according to this embodiment, further includes the step of additionally checking cardiac activity during each of a plurality of consecutive extension periods for an additional cardiac signal indicative of a potential arrhythmic cardiac event, and if an additional cardiac signal is detected during each of the plurality of consecutive extension periods, then the cardiac event is determined to be a hidden arrhythmia.

The relative refractory portion of the pace refractory period and/or the extension period are preferably adaptively varied in such a manner as to ensure detection of hidden arrhythmias despite variations in cardiac rate and/or pacing rate.

BRIEF DESCRIPTION OF THE DRAWINGS

These and various other objects, features, and advantages of the present invention will be readily understood from the following detailed description read in conjunction with the accompanying drawings, in which:

FIGS. 7A–7H and FIGS. 8A–8H depict waveforms and timing diagrams which are useful in understanding the method illustrated in FIG. 6.

DETAILED DESCRIPTION OF THE PREFERRED EMBODIMENTS

In overview, the present invention encompasses both improved methods for sensing arrhythmias in a pacemaker/defibrillator, and a pacemaker/defibrillator programmed to implement the same. In this connection, the specific type of pacemaker/defibrillator which is employed in the practice of the present invention is not limiting thereto. For example, any of the first, second, third or fourth types of dual-chamber pacemaker/defibrillators referred to hereinabove may be employed in the practice of the present invention. In this regard, the present invention encompasses three different methods for sensing arrhythmias in a pacemaker/defibrillator. Each of these methods is preferably implemented in detection software programmed into the microprocessor of the pacemaker/defibrillator in a manner which would be routine to a person of ordinary skill in the pertinent art in view of the present disclosure. For illustrative purposes, the following description of the dual-chamber pacemaker/defibrillator disclosed in the Pless et al. patent (U.S. Pat. No. 5,007,422) is provided, with the understanding that neither the type nor construction of the pacemaker/defibrillator employed in the practice of the present invention is limiting thereto.

Figure 1:
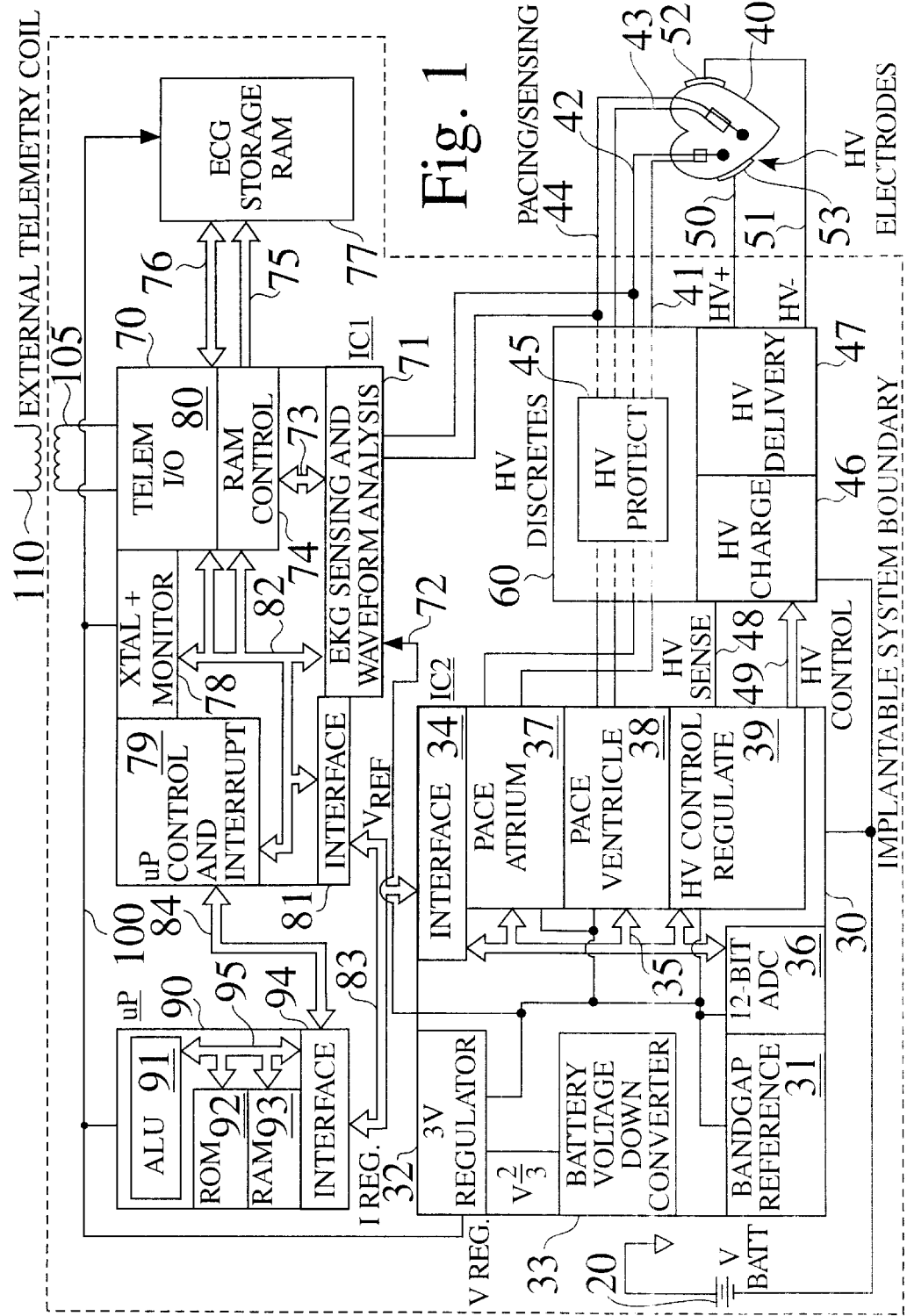
FIG. 1 is a block diagram of a conventional dual-chamber pacemaker/defibrillator.

With reference now to FIG. 1, there can be seen a block diagram of the dual-chamber pacemaker/defibrillator disclosed in the Pless et al. patent. In FIG. 1, the battery produces a positive voltage with respect to ground that varies from about 6.4 volts when new, to 5.0 volts at the end of service. The battery 20 directly powers IC2 30 and the high voltage discrete elements 60. Moreover, IC2 contains a band-gap reference circuit 31 that produces 1.235 volts, and 3 volt regulator 32 that powers the microprocessor 90, IC1 70, and the ECG storage RAM 77 through line 100. The regulator 32 runs off of a switched capacitor V battery voltage down converter 33 for improved efficiency.

The microprocessor 90 communicates with IC2 through a data and address bus 83 and an on-chip interface 34 that contains chip-select, address decoding and data bus logic as is typically used with microprocessor peripherals. The internal bus 35 allows the microprocessor to control a general purpose analog to digital converter (ADC) 36, atrial pace circuit 37, ventricular pace circuit 38, and HV control and regulate block 39. It will be appreciated that the ADC 36 is used by the microprocessor 90 to measure the battery and other diagnostic voltages within the device.

The atrial pace circuit 37 includes a digital to analog converter (DAC) that provides the ability to pace at regulated voltages. It communicates with the atrium of a heart 40 through two conductor wires. One conductor wire 41 is a switchable ground; the other conductor wire 42 is the pacing cathode and is also the input to the atrial sense amplifier, as will be described below. In addition, ventricular pace circuit 38, which also includes a DAC that provides the ability to pace at regulated voltages, communicates with the ventricle of a heart 40 through two conductor wires. One conductor wire 43 is a switchable ground; the other conductor wire 44 is the pacing cathode and is also the input to the ventricular sense amplifier, as discussed below. Advantageously, both the atrial and ventricular pace conductor wires pass through high voltage protection circuits 45 to keep the defibrillation voltages generated by the device from damaging the pacing circuits 37 and 38.

The HV control and regulate block 39 on IC2 30 is used by the microprocessor 90 to charge a high voltage capacitor included in the HV charge block 46 to a regulated voltage, and then to deliver the defibrillating pulse to the heart 40 through the action of switches in the HV delivery block 47. An HV sense line 48 is used by the HV regulation circuits 39 to monitor the defibrillating voltage during charging. An HV control bus 49 is used by the HV control circuits 39 to control the switches in the HV delivery block 47 for delivering the defibrillating pulse to the electrodes 52, 53 through conductor wires 50 and 51. It is noted that the electrodes are illustrated schematically as epicardial electrodes in FIG. 1 but that transvenous leads with endocardial electrodes are currently preferred.

IC1 70 is another microprocessor peripheral and provides timing, interrupt, telemetry, ECG storage, and sensing functions. In IC1, a dual channel electrogram (ECG) sensing and waveform analysis section 71 interfaces with the atrium and ventricle of the heart 40 through conductor wires 42 and 44 respectively. The sensed electrogram (ECG) is amplified and digitized. The amplifiers contained in this section 71 have multiple gain settings that are under microprocessor control for performing an automatic gain control (AGC) function. Features such as peak voltage and complex width are extracted by the waveform analysis circuits 71 for the microprocessor 90 to use in discriminating arrhythmias from normal sinus rhythm. The voltage reference 31 from IC2 30 is used by the digitizer circuit 71 in the usual fashion, and is supplied by line 72.

The digitized ECG is provided to the RAM controller 74 through a bus 73. The RAM controller sequences through the addresses of a static RAM 77 to maintain a pretrigger area, and this produces a post trigger area upon command from the microprocessor 90.

The crystal and monitor block 78 has a 100 kHz crystal oscillator that provides clocks to the entire system. The monitor is a conventional R-C oscillator that provides a back-up clock if the crystal should fail.

The microprocessor communicates with IC1 through two buses, 83 and 84. One bus 83 is a conventional data and address bus and goes to an on-chip interface 81 that contains chip select, address decoding and data bus drivers as are typically used with microprocessor peripherals. The other bus 84 is a control bus. It allows the microprocessor to set up a variety of maskable interrupts for events like timer timeouts, and sense events. If an interrupt is not masked, and the corresponding event occurs, an interrupt is sent from IC1 70 to the microprocessor 90 to alert it of the occurrence. On IC1 70, the up control and interrupt section 79 contains microprocessor controllable timers and interrupt logic.

The device can communicate with the outside world through a telemetry interface 80. A coil 105 is used in a conventional fashion to transmit and receive pulsed signals. The telemetry circuits 80 decode an incoming bit stream from an external coil 110 and hold the data for subsequent retrieval by the microprocessor 90. When used for transmitting, the circuit 80 receives data from the microprocessor 90, encodes it, and provides the timing to pulse the coil 105. The communication function is used to retrieve data from the implanted device, and to change the modality of operation if required.

The microprocessor 90 is of conventional architecture comprising an ALU 91, a ROM 92, a RAM 93, and interface circuits 94. The ROM 92 contains the program code that determines the operation of the device. The RAM 93 is used to modify the operating characteristics of the device as regards modality, pulse widths, pulse amplitudes, and so forth. Diagnostic data is also stored in the RAM for subsequent transmission to the outside world. The Algorithmic Logic Unit (ALU) 91 performs the logical operations directed by the program code in the ROM.

Certain conditions can arise in which an arrhythmia can be hidden by the pacing behavior of a dual chamber pacemaker/defibrillator. For example, these conditions can arise when the pacing cycle length (CL) is less than or equal to the minimum of either the tach/sinus cutoff multiplied by 2 or the defibrillator pace refractory period multiplied by 2. As an example, consider an arrhythmia of 300 ms CL that is initiated by a pace pulse. Assume also that the device is pacing at a CL of 600 Ms (100 ppm) and has a pace refractory period (RP) of approximately 350 ms. As long as the arrhythmia's rate is regular, the device will fail to sense the arrhythmia for an indefinite period of time due to the fact that all arrhythmic events fall into the pace RP.

Figure 2:
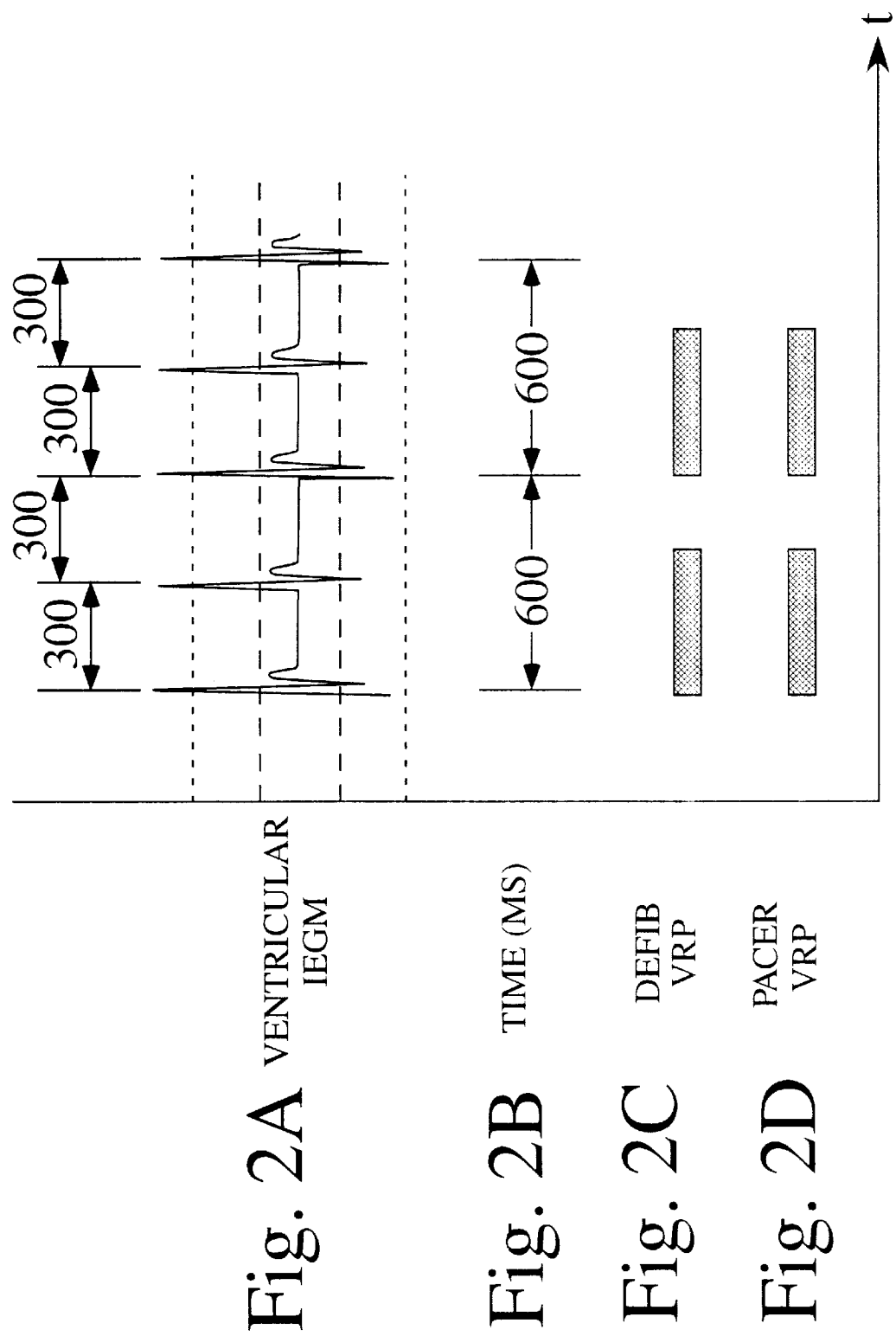
FIG. 2A illustrates an arrhythmic episode.
FIG. 2B illustrates the pacing pulses delivered by the dual-chamber pacemaker/defibrillator depicted in FIG. 1.
FIG. 2C illustrates the defibrillation pace refractory period (RP)
FIG. 2D illustrates the pace RP for the pacing pulses delivered in FIG. 2B.

It will be appreciated that this problem is a direct result of programming a pacing rate, pace refractory periods and non-sinus cutoff such that arrhythmias at certain rates cannot be detected due to the resultant short alert period. The hiding of a rhythm can occur when the pacing interval is twice the duration of the pace refractory period (RP). FIG. 2A depicts an exemplary ECG where this situation has occurred. In this case, the pacing rate is 100 bpm (600 ms; FIG. 2B), the defib pace refractory period is 400 ms (FIG. 2C), the pacer pace refractory period is 400 ms (FIG. 2D) and the hidden arrhythmia has an interval of 300 ms (FIG. 2A).

Figure 3:
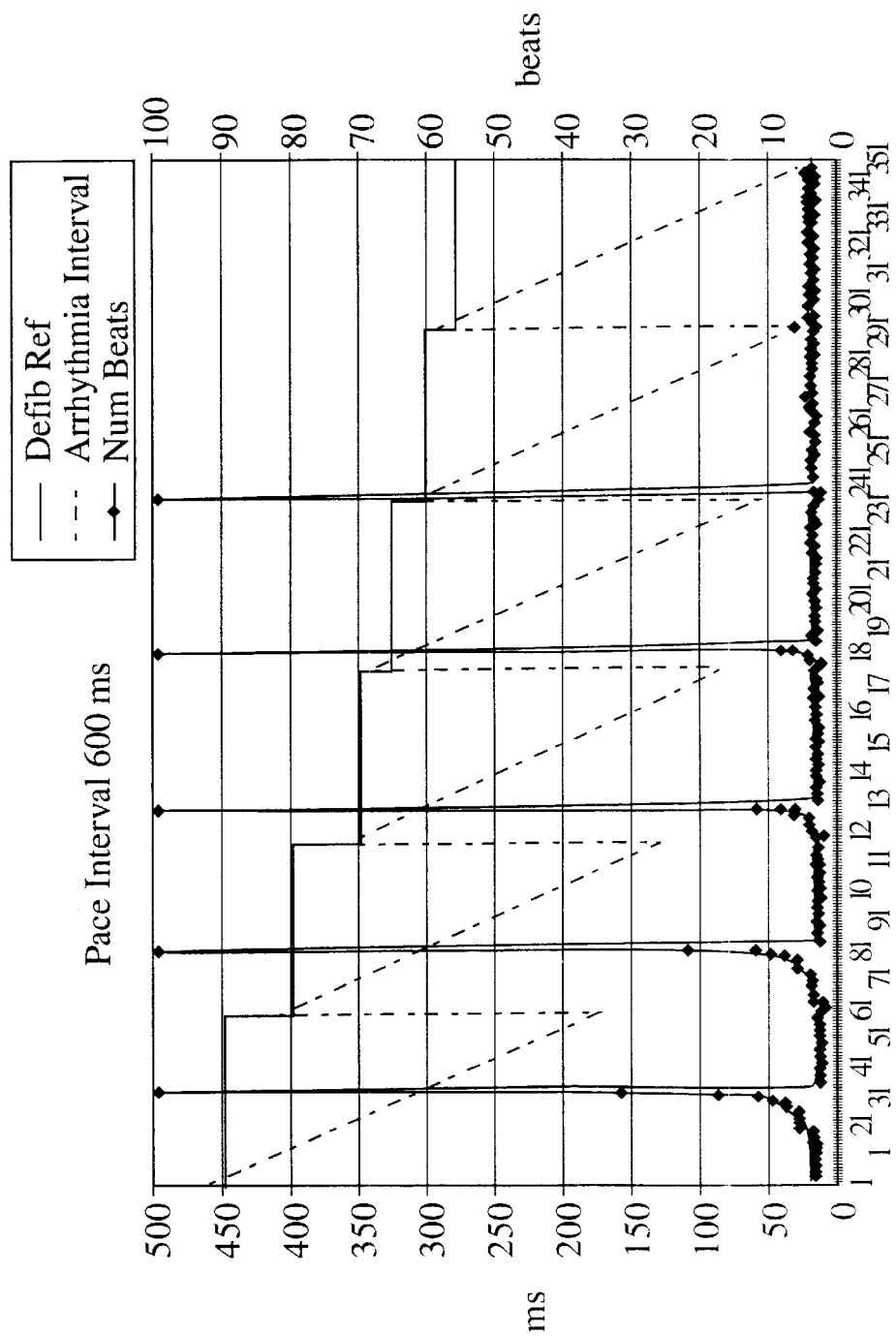
FIG. 3 is a graph illustrating the mechanism by which arrhythmias can remain undetected for appreciable lengths of time.

It should be noted that, depending on the selected pacing rate with respect to the pace refractory, the number of beats in which the arrhythmia may be hidden will vary. FIG. 3 shows how many intrinsic beats would be hidden by various pace refractory periods given a pacing interval of 600 ms (100 bpm). A score of 100 beats indicates that the intrinsic rhythm can remain hidden indefinitely. It should also be mentioned that FIG. 3 assumes that the worst case has occurred, i. e., that the pace pulse was coincident with the first beat of the arrhythmia.

From FIG. 3, it should be apparent that the amount of delay is inversely proportional to the amount of alert time available. In other words, as the alert period lengthens, the amount of time required to sense a single event decreases for each arrhythmic cycle length. The indefinitely hidden arrhythmia occurs at an arrhythmia interval of (a constant pace interval/2) ms for any pace refractory greater than pace interval/2. It should be noted that this condition can arise in any system where the pacing interval is allowed to be less than or equal to twice the pace RP.

It should be recognized that, in a system where the defibrillator and pacemaker have different sensing thresholds or different refractory periods, the condition can occur much more often. In a system with the same thresholds and refractory periods, the condition can only occur if the onset of the arrhythmia occurs during the pace RP. In a system with either of the other two above-mentioned properties, the condition can be induced easily by having the pacer miss an event due to the established refractory period or sensing threshold and by inadvertently pacing into the arrhythmia.

In a dual-chamber pacemaker/defibrillator of the first type (i.e., same sensing, same sense RPs), one only has to ensure that one intrinsic event from the masked arrhythmia is detected by the device to guarantee further successful sensing of the arrhythmia. It should be noted that this assumes that the sense RP is short, as it must be in this environment for successful arrhythmia detection. Successful detection of an arrhythmia can be accomplished by lengthening the pace CL by a small amount for a number of cycles followed by a shortening of the pace CL for the same number of cycles giving an average pacing rate equivalent to the desired rate. This advantageously could occur at all times but, preferably, it would occur only when conditions make arrhythmia masking possible. From the discussion above, it should be recognized that changing the pace CL by a small amount over a number of cycles will move the arrhythmia and paced rhythm out of synchronization. The method according to a first preferred embodiment of the present invention is based upon these discoveries.

Figure 4A:
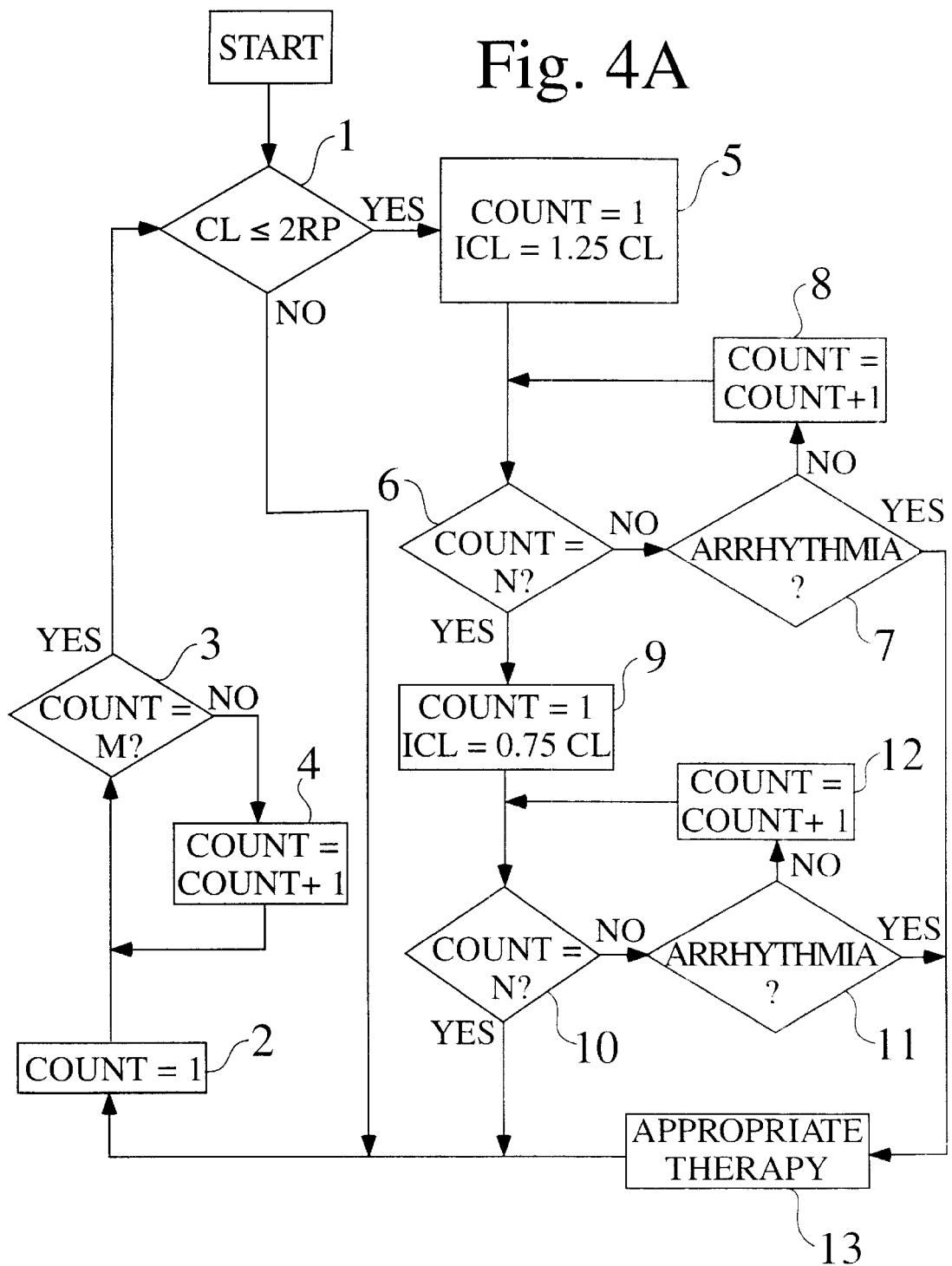
FIG. 4A is a flowchart of a method for detecting arrhythmias according to a first embodiment of the present invention and FIGS. 4B and 4C illustrate the respective average and specific cycle lengths of a series of pacing pulses.
Figure 4B:
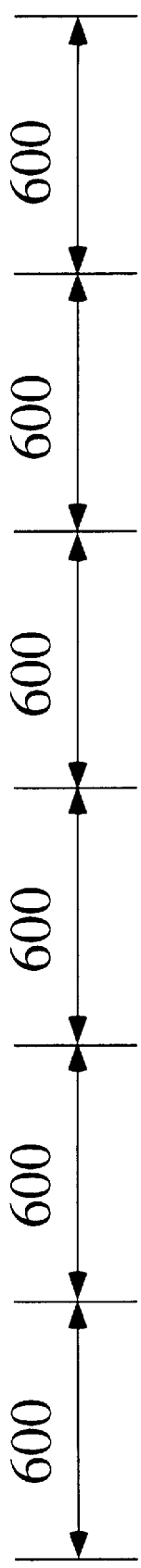
Figure 4C:

The method according to a first embodiment of the present invention will best be understood by referring to the flowchart of FIG. 4A in conjunction with the respective average and specific cycle lengths of a series of pacing pulses illustrated in FIGS. 4B and 4C.

As shown in FIG. 4A, the method advantageously may begin with a check to determine if conditions exist whereby an arrhythmia can be masked by a series of applied pacing pulses of a predetermined cycle length (CL). In the exemplary case illustrated in FIG. 4B, the predetermined CL is 600 ms and a check is performed in step 1 to determine whether the CL is less than or equal to the minimum of either the tach/sinus cutoff multiplied by 2 or the defibrillator pace refractory period (RP) multiplied by 2. If the answer is negative, the determination procedure jumps to steps 2–4 to execute a delay function before repeating the check of step 1. In an exemplary case, step 2 sets a count value equal to 1 and then checks at step 3 to see whether the count value is equal to a predetermined delay value M, where M indicates a count value needed to delay the execution of step 1 by a desired time. It should be mentioned that M advantageously can be an integer 1; when M is equal to 1, the check of step 1 is repeated continuously. If the answer is negative, the count value is incremented by 1 in step 4 and step 3 is repeated until the answer is positive. When the determination at step 3 is positive, step 1 is repeated.

If the answer at step 1 is positive, indicating that conditions are ripe for allowing hidden arrhythmias, a count value is set equal to 1 and the instantaneous cycle length (ICL) is set to 1.X times CL, where X is a decimal, in step 5. Preferably, the difference between ICL and CL is small, although it should be noted that ICL increases over CL by 25% in FIG. 4C for purposes of illustration. At step 6, a test is performed to determine whether the count value is N where N indicates the number of times the established ICL value is to be used. If the answer is negative, arrhythmia detection is performed. In the event that an arrhythmia is detected at step 7, the program jumps to step 13 and initiates a predetermined therapy and then jumps to step 2. However, if an arrhythmia is not detected, the program increases the count value by 1 during step 8 and then repeats step 6. Steps 6–8 are repeated until either Count=N or an arrhythmia is detected.

In the event that the answer at step 6 is positive, the count value is reset to 1 and the value of ICL is reset to (1.0–X) times CL. In the exemplary case illustrated in FIG. 4C, an exaggerated ICL of 450 ms is used. Then, the loop formed by steps 10–12 are performed until either COUNT=N is true or an arrhythmia is detected. If an arrhythmia is detected, step 13 is executed; if COUNT=N, step 2 is performed.

In a dual-chamber pacemaker/defibrillator of the third type (i.e., same sensing, different sense RPs), one has to cause at least one arrhythmic sense event to fall into the pacer's alert period and cause the pacer to continue sensing the arrhythmia successfully after this sensed event. The first goal, i.e., to unmask the arrhythmia, advantageously can be accomplished by lengthening the pace CL by a small amount for a number of cycles followed by a shortening of the pace CL for the same number of cycles giving an average pacing rate equivalent to the desired rate. This could occur at all times or it could occur only when conditions make arrhythmia masking possible. Changing the pace CL by a small amount over a number of cycles will advantageously move the arrhythmia and paced rhythm out of synchronization. Forcing the pacer to continue sensing the arrhythmia can be accomplished by insuring that the pacer's sense RP is less than one half of the pacing CL. This can be done by constraining the programming of that value to one half the minimum pacing CL or using an adaptive sense RP. An adaptive sense RP shortens as the pacing CL or intrinsic CL shortens. The method according to a second preferred embodiment of the present invention is based upon these discoveries.

Figure 5A:
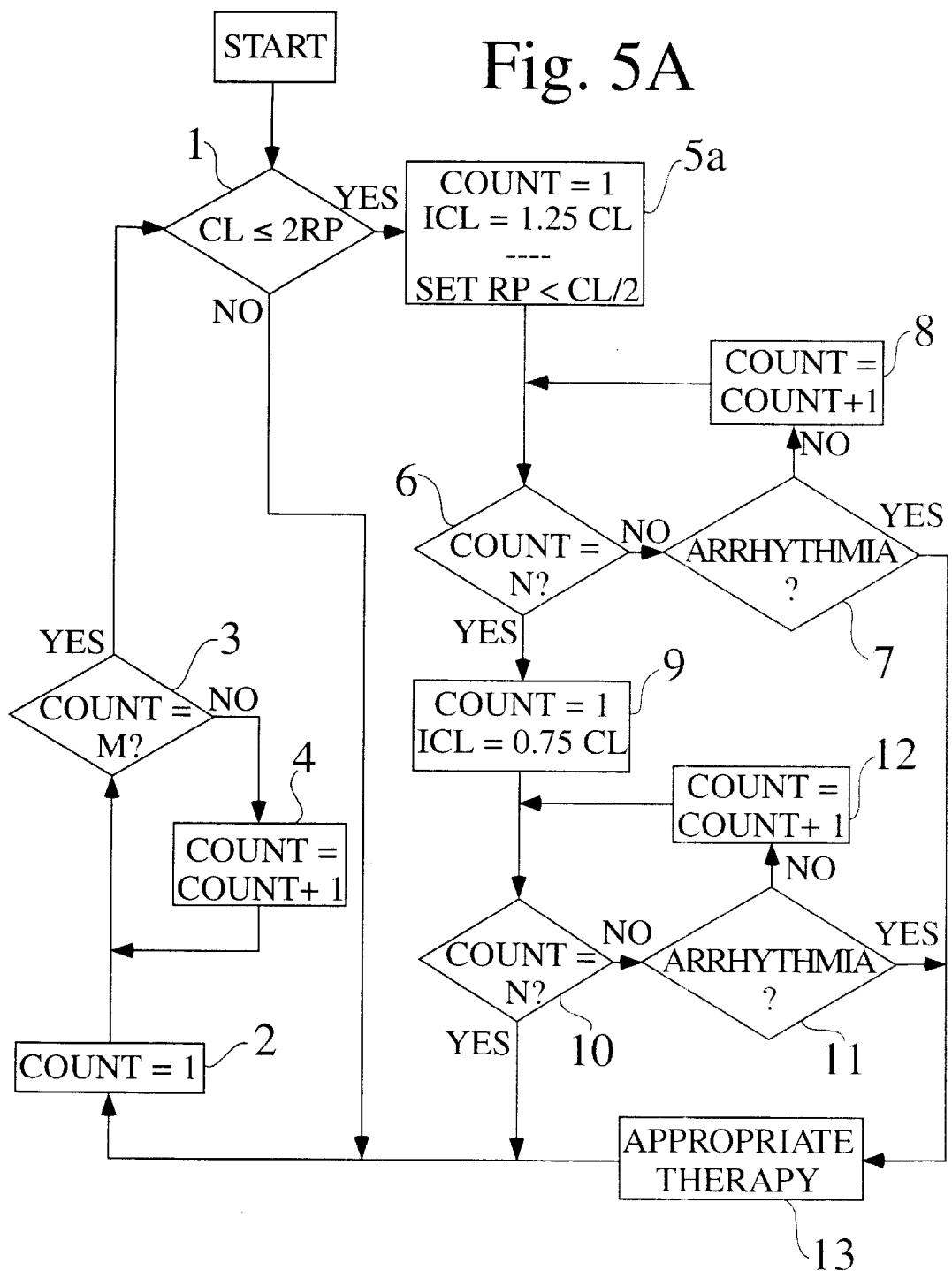
FIG. 5A is a flowchart of a method for detecting arrhythmias according to a second embodiment of the present invention and FIGS. 5B and 5C depict the average and specific cycle lengths, respectively, of a series of pacing pulses.
Figure 5B:
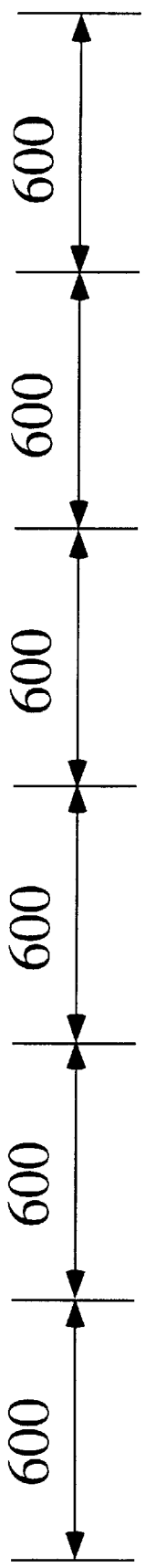
Figure 5C:
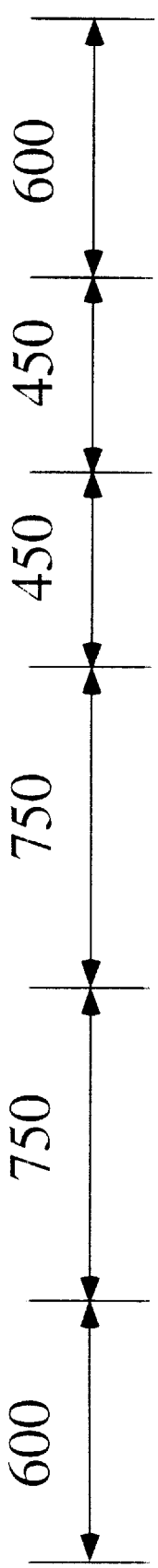

The method according to the second embodiment of the present invention can best be understood by referring to the flowchart of FIG. 5A in conjunction with the respective average and specific cycle lengths of a series of pacing pulses illustrated in FIGS. 5B and 5C. A detailed description of FIGS. 5A–5C will be omitted, since the principal difference between FIGS. 4A and 5A is step 5a, wherein the count value is set to 1, the ICL is set to (1.0+X) times CL and, additionally, the pacer sense RP is constrained to be less than CL/2 ms.

In a dual-chamber pacemaker/defibrillator of the second and fourth types (i.e., both utilizing different sensing with same or different sense RPs), one has to cause at least one arrhythmic sense event to fall into the pacer's alert period and, subsequently, allow detection of the arrhythmia without inhibiting pacing substantially, e.g., when noise or some other extraneous signal could be classified as arrhythmia. The hidden arrhythmia can be detected by periodically checking a relative refractory portion of the pace RP to see if a signal indicative of arrhythmia can be detected. This relative refractory period is produced by shortening the established RP by the calculated Adaptive Relative Refractory (ARR) period. It will be appreciated that the reason this period is adaptive is that the amount of time needed to see any 2:1 (with respect to the pace RP) rhythm is dependent on the current pace interval and pace refractory period. It should be noted that this method only needs be employed when the pacing interval has decreased to the point where the CL is less than or equal to twice the pace refractory (or non-sinus cutoff, if this is shorter).

The use of the ARR period (ARRP) would be indicated and applied by the occurrence of a programmed number of consecutive pace pulses at a pacing interval which is twice the pace RP or less. Advantageously, the physician may elect to use 1 as the programmed number, which disables the delay function. The triggering condition calculation advantageously could be made to involve the sinus/tach cutoff, as would be readily appreciated by one of ordinary skill in the art. Use of the ARRP may not be needed if paced intervals are irregular enough to prevent hiding of a regular arrhythmia. Use of the ARRP may not be needed if the ARRP is significantly smaller than an arrhythmic complex, e.g. 10–30 milliseconds. The method according to the third preferred embodiment of the present invention is based upon these discoveries.

Figure 6:
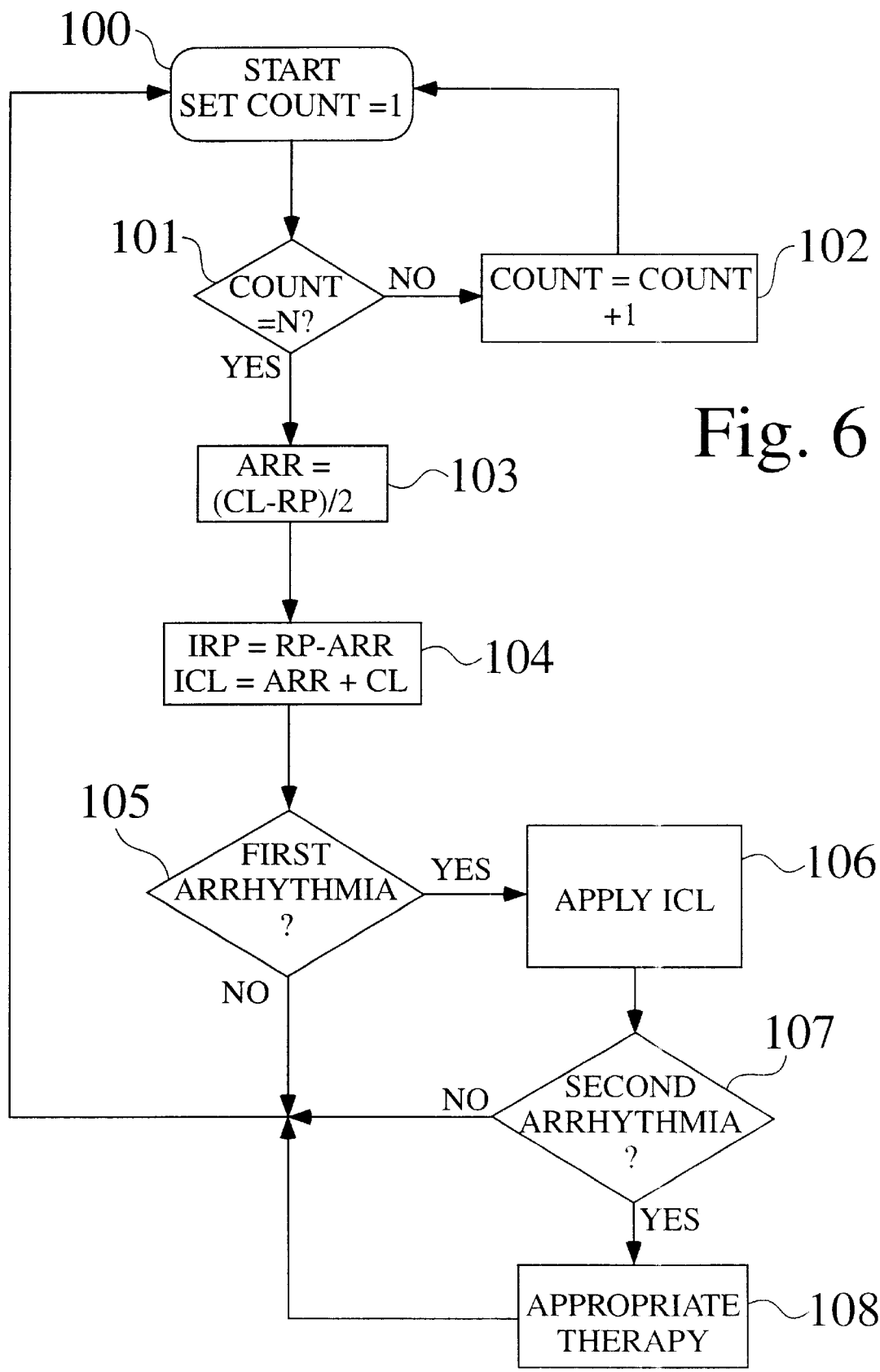
FIG. 6 is a flowchart of a method for detecting arrhythmias according to a third preferred embodiment of the present invention.
Figure 7E:
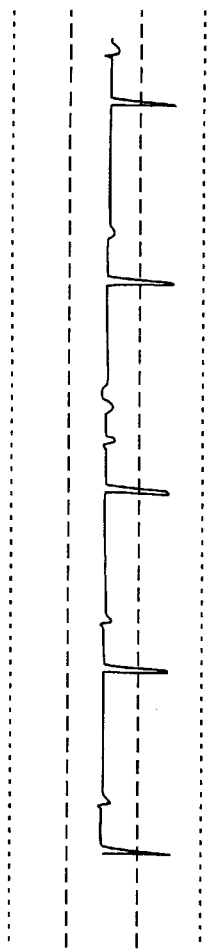
Figure 7F:
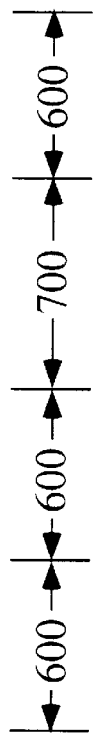
Figure 7G:
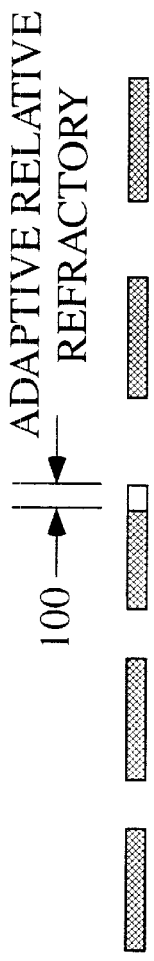
Figure 7H:

Referring to FIG. 6, at the start of the detection method according to the third embodiment of the present invention, a count value is set to an initial value (step 100) and then a check is performed to determine whether the count value is equal to a predetermined number N during step 101. This count represents the number of consecutive pace pulses all occurring at pacing intervals which allow masking of an arrhythmia. If the answer is negative, the count value is incremented by 1 in step 102 and then step 101 is repeated. If the answer is affirmative, the program advances to steps 103 and 104 to calculate values indicative of the decrease in the defibrillator RP and the associated delay in the next pace pulse.

Preferably, the starting value of the ARR period is determined by the expression pace RP−(pace CL/2) ms. During step 104, an immediate refractory period (IRP), which will be used during only one pacing period, by subtracting ARR from RP, i.e., IRP=RP−ARR. Preferably, an additional calculation is also performed to determine the instantaneous cycle length by extending the pace CL by the ARRP value, i.e., ICL=ARR+CL. It should be mentioned that this is actually a worst case extension of the pace pulse. For the exemplary cases shown in FIGS. 7A–7H and 8A–8H, CL is 600 ms, RP is 400 ms, the ARR is 100 ms, the IRP is 300 ms and the ICL is 700 ms.

During step 105, a check is performed for an arrhythmia using the IRP value determined in step 104. See FIGS. 7C, 7G, 8C and 8G. If no arrhythmia event is seen following the IRP during step 105, the program returns to step 100 and, thus, pacing continues unaltered. However, if a signal indicative of arrhythmia is sensed during step 105, the next pace pulse will be delayed by the duration of the ARR period by applying the ICL during step 106. For an exemplary case shown in FIGS. 7F, 8B and 8F, CL is 600 ms and ICL is 700 ms. The overall effect of a negative response to step 105 in the method of FIG. 6 is illustrated in FIGS. 7A–7D, which collectively depict the case where no arrhythmia is present and no T wave is detected. In this exemplary case, the pace interval has triggered the use of the ARR period, but there is no arrhythmia to be detected. Additionally, no T wave is sensed during the ARR period and, thus, the pacing interval, i.e., CL, remains unchanged. In contrast, an affirmative response to step 105 could result in the situations illustrated in FIGS. 7E–7H and 8A–8D.

During step 107, a check is made for a second arrhythmia. If the answer is negative, the program jumps to step 100 to restart the program. In the event that a second arrhythmia is sensed during step 107, appropriate therapy is applied. In the latter case, an arrhythmia was hidden by the pace refractory period. The ARR period uncovers the arrhythmia and both the pacer and defib circuitry sense the second complex after uncovering the arrhythmia.

It should again be mentioned that ICL is actually a worst case extension of the pace pulse. The extension could be adaptive as well and, theoretically, only needs to be as long as the elapsed time between the end of the IRP and the occurrence of the sensed signal. However, waiting out the entire CL extension, i.e., the added ARR period, is the conservative approach. Moreover, the use of the entire ICL simplifies the program software. Advantageously, the pacemaker/defibrillator may be programmed to detect and count a number of events in consecutive ARR periods before the pacing CL is temporarily modified.

It should also be mentioned that the purpose of the extension is to determine if the signal seen in the Adaptive Relative Refractory is actually a T wave. If another sensed event occurs during the extended CL period, it is likely to be from a hidden arrhythmia and is certainly not another T wave. Moreover, it should be noted that the size of the extension corresponds to the slowest arrhythmia that may be hidden by a pace refractory period. If a signal is sensed during the ARR period and another signal is not seen during the pace extension, pacing will continue unaltered after the delayed pace pulse until the mechanism is re-triggered in steps 100–102.

If a second signal is seen during the extended CL, the next action is dependent on the type of ICD. In the first type of ICD (both the pacer and defibrillator have the same sensing front end and the same refractory periods), nothing else needs to be done as the pacer would have seen the second event and inhibited pacing. The sense refractory period now should be short enough to detect the next arrhythmic sense event. In the third type of ICD, the pacer will see the arrhythmic sense event but some measure must be taken to insure that the pacer sense RP is short enough for continued sensing of the arrhythmia. This requires that the pacer sense RP meet the restriction of being less than half the current pacing CL. In ICDs of the second and fourth types, the pacer may or may not have seen the second sense event. If the pacer did see the sense event then pacing will be inhibited and the pacer sense RP must be less than half the current pacing CL to insure continued sensing of the arrhythmia. If the pacer did not see the sense event, a safety pace pulse should be delivered shortly after the sense event. The Adaptive Relative Refractory period should again be used to assure that the defib machine sees the next arrhythmic event. Additionally, the MTR and MSR should be decreased so that the pacing interval/2 is greater than the pace refractory. Slowing these rates will assure that the defibrillator will see the arrhythmia with at least 2 intervals to 1 pace pulse, in the event that the pacer is completely undersensing.

The continued use of the ARR period advantageously can insure detection of the arrhythmia complex which ordinarily would have been hidden by the pace refractory. If the pacer continues to pace at the reduced pacing rate for several intervals without the defibrillator seeing sensed events, pacing may revert back to the previous state. The short sense to pace intervals created when the pacer is completely undersensing the arrhythmia must be handled by either ignoring those intervals or preventing the short sense to pace from occurring.

A troublesome case occurs when a PVC is detected in the ARR period and a subsequent T wave is detected as well. If no T wave were detected, the outcome would be exactly as if only a T wave were sensed during the ARR period. When the T wave is sensed, this introduces periodic short intervals in the defibrillator. This may or may not be a problem depending on how often the ARR period is triggered and how frequent PVCs are being detected during this period. Thus, a system with different sensing for the pacer and defibrillator, safety pacing into the T wave of a PVC needs to be considered. Advantageously, a slight delay in the safety pace should be sufficient to negate the problem, e.g., as depicted in FIGS. 8E–8H.

It should be mentioned that although the present invention has been described in terms of an exemplary device using a microprocessor, the present invention is not so limited. The inventive method may be carried out by any form of circuitry. Moreover, the pacemaker/defibrillator according to the present invention advantageously may employ either analog or digital control circuitry capable of carrying out the disclosed functions in the required sequence. Preferably, the control circuitry is a microprocessor, but other circuitry such as a digital signal processor or a programmable logic device can also be used.

It should also be mentioned that other methods and circuitry for detecting arrhythmias may be employed without departing from the spirit and scope of the present invention. For example, the endpoint of an absolute refractory period could be actively determined by, for example, a comparator, which could be included to sense the afterpotential; the refractory period would end when the sensed afterpotential fell below a predetermined threshold.

Although several presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A method of detecting an arrhythmia hidden by pacing in a pacemaker/defibrillator, comprising the steps of:

periodically checking cardiac activity during a relative refractory portion of a pace refractory period for a cardiac signal indicative of a potential arrhythmic cardiac event;

if a cardiac signal is detected during the periodically checking step, then checking cardiac activity during the relative refractory portion of each of a plurality of consecutive pace refractory periods for a further cardiac signal indicative of a potential arrhythmic cardiac event; and, if a further cardiac signal is detected during at least a minimum number of the plurality of consecutive pace refractory periods, then delaying a next occurring pacing pulse by an extension period.

2. The method as set forth in claim 1, further comprising the step of additionally checking cardiac activity during the extension period for an additional cardiac signal indicative of a potential arrhythmic cardiac event.

3. The method as set forth in claim 2, wherein if a cardiac signal is detected during the extension period, then the cardiac event is determined to be a hidden arrhythmia.

4. The method as set forth in claim 2, further comprising the step of, if a cardiac signal is not detected during the extension period, then delivering the next occurring pacing pulse without any delay.

5. The method as set forth in claim 2, further comprising the step of adaptively varying the extension period in such a manner as to ensure that the extension period is at least as long as the relative refractory portion of the preceding pace refractory period.

6. The method as set forth in claim 1, further comprising the step of additionally checking cardiac activity during each of a plurality of consecutive extension periods for an additional cardiac signal indicative of a potential arrhythmic cardiac event, and if an additional cardiac signal is detected during the minimum number of the plurality of consecutive extension periods, then the cardiac event is determined to be a hidden arrhythmia.

7. The method as set forth in claim 1, wherein the step of periodically checking is initiated in response to detection of a trigger condition that makes arrhythmia masking possible.

8. The method as set forth in claim 7, wherein the trigger condition comprises a pace cycle length being less than or equal to the minimum of either a tach/sinus cutoff multiplied by 2 or a defibrillator pace refractory period multiplied by 2.

9. The method as set forth in claim 1, wherein the extension period is sufficiently long to ensure detection of a slowest arrhythmia that may be hidden by pacing.

10. The method as set forth in claim 1, wherein the extension period is adaptively varied.

11. The method as set forth in claim 1, wherein the relative refractory portion of the pace refractory period is adaptively varied.

* * * * *